(12) United States Patent
Li et al.

(10) Patent No.: US 8,932,446 B1
(45) Date of Patent: Jan. 13, 2015

(54) ACTINIDE-ION SENSOR

(71) Applicants: Shelly X Li, Idaho Falls, ID (US);
Jan-fong Jue, Idaho Falls, ID (US);
Ronald Scott Herbst, Idaho Falls, ID (US);
Steven Douglas Herrmann, Idaho Falls, ID (US)

(72) Inventors: Shelly X Li, Idaho Falls, ID (US);
Jan-fong Jue, Idaho Falls, ID (US);
Ronald Scott Herbst, Idaho Falls, ID (US);
Steven Douglas Herrmann, Idaho Falls, ID (US)

(73) Assignee: U.S. Department of Energy, Washington, DC (US)

( * ) Notice: Subject to any disclaimer, the term of this patent is extended or adjusted under 35 U.S.C. 154(b) by 111 days.

(21) Appl. No.: 13/891,308

(22) Filed: May 10, 2013

(51) Int. Cl.
*G01N 27/333* (2006.01)
*G01N 27/26* (2006.01)

(52) U.S. Cl.
CPC .................................. *G01N 27/26* (2013.01)
USPC .......................................... 204/419; 204/416

(58) Field of Classification Search
USPC ................................ 204/416–420; 205/789.5
See application file for complete search history.

(56) References Cited

U.S. PATENT DOCUMENTS 3,864,233 A * 2/1975 Dietrich et al. ............... 204/418
4,801,371 A * 1/1989 Shiga et al. .................. 204/418

FOREIGN PATENT DOCUMENTS

JP 09-89833 A * 4/1997 ........... G01N 27/333

OTHER PUBLICATIONS

JPO computer-generated English language translation of Aoyanagi et al. JP 09-089833 A.*
Duncan et al. "Application of calixarene ionophores in PVC based ISEs for uranium detection," Sensors and Actuators B 73 (2001) 228-235.*
Ganjali et al. "Highly selective and sensitive Th4+ -PVC-based membrane sensor based on 2-(diphenylphosphorothioyl)-N',N'-diphenylacetamide," J. Appl. Electrochem. (2007) 37:827-833.*

* cited by examiner

*Primary Examiner* — Alex Noguerola
(74) *Attorney, Agent, or Firm* — Michael J. Dobbs; Daniel D. Park; John T. Lucas

(57) ABSTRACT

An apparatus for the real-time, in-situ monitoring of actinide-ion concentrations. A working electrolyte is positioned within the interior of a container. The working electrolyte is separated from a reference electrolyte by a separator. A working electrode is at least partially in contact with the working electrolyte. A reference electrode is at least partially in contact with the reference electrolyte. A voltmeter is electrically connected to the working electrode and the reference electrode. The working electrolyte comprises an actinide-ion of interest. The separator is ionically conductive to the actinide-ion of interest. The separator comprises an actinide, Zr, and Nb. Preferably, the actinide of the separator is Am or Np, more preferably Pu. In one embodiment, the actinide of the separator is the actinide of interest. In another embodiment, the separator further comprises P and O.

20 Claims, 4 Drawing Sheets

US 8,932,446 B1

ACTINIDE-ION SENSOR

GOVERNMENT INTERESTS

The United States Government has rights in this invention pursuant to Contract No. DE-AC07-05ID14517, between the U.S. Department of Energy (DOE) and Battelle Energy Alliance.

FIELD OF THE INVENTION

One embodiment of the present invention relates to a real-time, in-situ sensor for monitoring actinide-ion concentration in an electrolyte. Preferably, the actinide-ion is plutonium ion and the electrolyte is an aqueous electrolyte. In a preferred embodiment, the actinide-ion concentration is monitored during the aqueous separation of spent nuclear fuel.

BACKGROUND OF THE INVENTION

Nuclear reactors are becoming an increasingly necessary means of meeting the nation's energy requirements given growing concerns about traditional carbon producing methods of generating energy. A principal concern prior to the acceptance of nuclear energy is the safe management of radioactive waste during reprocessing and storage. Therefore, there exists a need for in-situ, real-time monitoring of actinide-ion concentrations in aqueous solutions.

SUMMARY OF THE INVENTION

An apparatus for the real-time, in-situ monitoring of actinide-ion concentrations which comprises a working electrode, a reference electrode, a container, a working electrolyte, a separator, a reference electrolyte, and a voltmeter. The working electrolyte is positioned within the interior of the container. The working electrolyte is separated from the reference electrolyte. The separator at least partially separates and contacts the working electrolyte and the reference electrolyte. The working electrode is at least partially in contact with the working electrolyte. The reference electrode is at least partially in contact with the reference electrolyte. The voltmeter is electrically connected to the working electrode and the reference electrode. The working electrolyte comprises an actinide-ion of interest. The separator is ionically conductive to the actinide-ion of interest. The separator comprises an actinide, Zr, and Nb. The reference electrolyte comprises the actinide-ion of interest with a known concentration. The voltmeter comprises a means for measuring the voltage between the working electrode and the reference electrode. The voltmeter comprises a means for indicating the concentration of the actinide-ion of interest within the working electrolyte. Preferably, the actinide of the separator is Am or Np, more preferably Pu. In one embodiment, the actinide of the separator is the actinide of interest. In another embodiment, the separator further comprises P and O.

DETAILED DESCRIPTION OF THE INVENTION

An apparatus for the real-time, in-situ monitoring of actinide-ion concentrations which comprises a working electrode, a reference electrode, a container, a working electrolyte, a separator, a reference electrolyte, and a voltmeter. The working electrolyte is positioned within the interior of the container. The working electrolyte is separated from the reference electrolyte. The separator at least partially separates and contacts the working electrolyte and the reference electrolyte. The working electrode is at least partially in contact with the working electrolyte. The reference electrode is at least partially in contact with the reference electrolyte. The voltmeter is electrically connected to the working electrode and the reference electrode. The working electrolyte comprises an actinide-ion of interest. The separator is ionically conductive to the actinide-ion of interest. The separator comprises an actinide, Zr, and Nb. The reference electrolyte comprises the actinide-ion of interest with a known concentration. The voltmeter comprises a means for measuring the voltage between the working electrode and the reference electrode. The voltmeter comprises a means for indicating the concentration of the actinide-ion of interest within the working electrolyte. Preferably, the actinide of the separator is Am or Np, more preferably Pu. In one embodiment, the actinide of the separator is the actinide of interest. In another embodiment, the separator further comprises P and O.

FIG. 1

Figure 1:
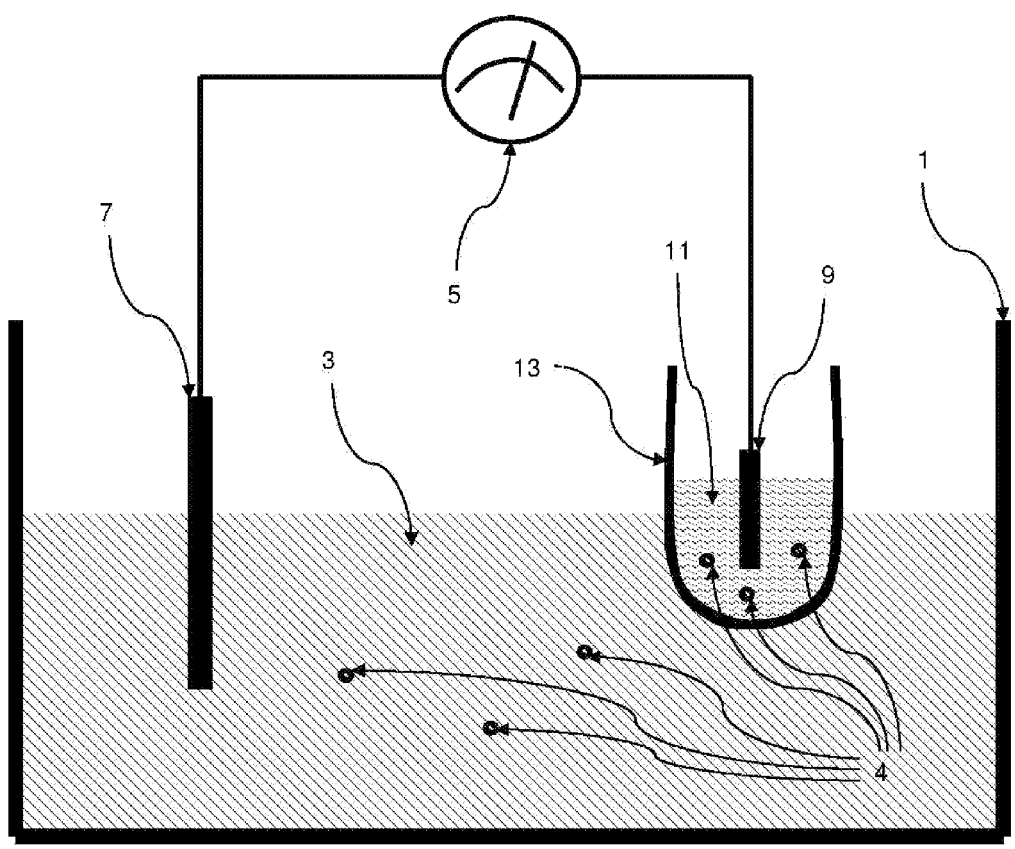
FIG. 1 shows a cross sectional view of one embodiment of an actinide-ion sensor.

FIG. 1 shows a cross sectional view of one embodiment of an actinide-ion sensor. Shown is a container 1 and a working electrolyte 3 within the container. The working electrolyte 3 comprises an actinide-ion of interest 4. Additionally, a voltmeter 5 is electrically connected to a working electrode 7 and a reference electrode 9. The working electrode 7 at least partially contacts the working electrolyte 3. Preferably, the working electrode 7 is at least partially submerged in the working electrolyte 3, more preferably, the majority of the working electrode 7 is submerged in the working electrolyte 3.

The reference electrode 9 at least partially contacts a reference electrolyte 11. Preferably, the reference electrode 9 is at least partially submerged in the reference electrolyte 11, more preferably, the majority of the reference electrode 9 is submerged in the reference electrolyte 11. The reference electrolyte 11 comprises the actinide-ion of interest 4.

The reference electrolyte 11 is separated from the working electrolyte 3 by a separator 13. The separator 13 at least partially contacts both the working electrolyte 3 and the reference electrolyte 11. The separator 13 is preferably at least partially submerged in the working electrolyte 3, more preferably, the majority of the separator 13 is submerged in the working electrolyte 3. The separator 13 comprises an actinide, Zr, and Nb. The separator 13 conducts the actinide-ion of interest 4 between the working electrolyte 3 and the reference electrolyte 11. The voltmeter 5 measure the voltage between the reference electrode 9 and the working electrode 7.

Container 1

The container 1 comprises any material that does not substantially react with the working electrolyte 3. Preferably, the material does not substantially react if the material is used continually for over one year without damage or need of repair or replacement of equipment. More preferably, the container 1 is stainless steel.

Working Electrolyte 3

The working electrolyte 3 is any substance comprising free ions of the actinide of interest 4. Preferably, the working electrolyte 3 is an acidic aqueous solution, preferably nitric acid having free ions of an actinide of interest 4, preferably Am, Np, Pu and U.

Actinide-Ion of Interest 4

The actinide-ion of interest 4 is an ion or charged molecule preferably comprising at least one of the elements in spent nuclear fuel, which include: Th, U, Np, Pu, Am, and Cm. Preferably, the actinide-ion of interest 4 is Np, Pu, and Am. More preferably, the actinide-ion of interest 4 is Pu.

Voltmeter 5

The voltmeter 5 is any device used to determine or indicate the voltage across the working electrode 7 and reference electrode 9, which is related to the concentration of actinide-ion of interest 4 in the working electrolyte 3. Exemplary embodiments of the voltmeter 5 include a multimeter, a potentiometer, a galvanometer, an oscilloscope, and an analog-to-digital converter. Preferably, the voltmeter 5 comprises one or more electrical components, more preferably a central processing unit, microcontroller, application specific integrated circuit (ASIC), an analog-to-digital converter, a voltage comparator or combinations thereof. In a preferred embodiment, the voltmeter 5 is an analog-to-digital converter connected to a microcontroller/central-processing-unit (CPU) having a display (e.g. FIG. 3). In an alternative embodiment, the voltmeter 5 is an electrical circuit configured to output light in relation to voltage across the working electrode 7 and reference electrode 9 (e.g. FIG. 4). Preferably, the voltmeter 5 provides a high-impedance across the working electrode 7 and reference electrode 9 as close to an open circuit (infinite impedance) as possible, to prevent any electrical current between the working electrode 7 and the reference electrode 9.

Working Electrode 7

The working electrode 7 is made from any electrically conductive material which is not substantially reactive with the working electrolyte 3. Preferably, the material is not substantially reactive if the material is used continually for over one year without damage or need of repair or replacement of equipment. More preferably, the working electrode 7 is made of Ta, W, Pt, or a combination thereof.

Reference Electrode 9

The reference electrode 9 is made from any electrically conductive material which is not substantially reactive with the ionic environment of the reference electrolyte 11. Preferably, the material is not substantially reactive if the material is used continually for over one year without damage or need of repair or replacement of equipment. More preferably, the reference electrode 9 is made of Ta, W, Pt, or a combination thereof.

Reference Electrolyte 11

The reference electrolyte 11 is a compound or solution with a known concentration of the actinide-ion of interest 4. Preferably, the reference electrolyte 11 is any substance comprising free ions of the actinide of interest 4. In one embodiment, the reference electrolyte 11 comprises aqueous solutions with known Pu ion concentrations. In yet another alternative embodiment, the reference electrolyte 11 may further comprise a nitric acid solution with dissolved Pu or actinides.

Separator 13

The separator 13 is made into a configuration sufficient to separate the reference electrolyte 11 from the working electrolyte 3 and ionically conductive to the actinide-ion of interest 4. Ionically conductive refers to ionic conduction of the actinide-ion of interest 4 through all, or a portion, of the separator 13. Preferably, the separator 13 has an ionic conductivity to the actinide-ion of interest 4 greater than $10^{-6}$ S/cm. Preferably, the separator 13 is made into a tube with a single closed end. In an alternative embodiment, the separator 13 is made from a disk cemented to one open end of a tube. Other shapes and configuration may also be used. Preferred embodiments encompass a separator 13 made from a plurality of portions, whereby one or more of the plurality of portions are ionically conductive to the actinide-ion of interest 4.

The separator comprises an actinide, Zr, and Nb. More preferably, the separator comprises the actinide of interest, Zr, and Nb. In another embodiment, the separator comprises the actinide of interest, Zr, Nb, P and O. In a preferred embodiment, the separator consists essentially of an actinide (preferably Am, Np or the actinide of interest, more preferably Pu), Zr, and Nb. In a preferred embodiment, the separator consists of an actinide (preferably Am, Np or the actinide of interest, more preferably Pu), Zr, and Nb. In a preferred embodiment, the separator consists essentially of an actinide (preferably Am, Np or the actinide of interest, more preferably Pu), Zr, Nb, P and O. In a more preferred embodiment, the separator consists of an actinide (preferably Am, Np or the actinide of interest, more preferably Pu), Zr, Nb, P and O.

The separator is preferably produced by mixing the actinide, Zr, and Nb into a solution, preferably also further comprising P and O. The resulting solution is then mixed with ethanol, first dried, calcinated, milled, second dried, die-pressed and sintered. Preferably, the solution is mixed in ethanol for at least 24 hours at 200 rpm or more. Preferably, the calcination is at 1,000 to 1,300° C. for at least 12 hours. Preferably, the milling is 80 rpm or more for at least 24 hours. Preferably the die pressing is at 6,000 psi or more. Preferably the sintering is at least 1,300° C. for 24 hours or more. Preferably, the separator has the formula $A_xZr_yNb(PO_4)_3$, where A is the actinide, preferably Am, Np, or the actinide of interest, more preferably Pu. In a preferred embodiment, the separator has the formula $A_xZr_yNb(PO_4)_3$. In another embodiment, the separator has the formula $A_xZr_yNb$, where A is the actinide, preferably Am, Np, or the actinide of interest, more preferably Pu.

Exemplary Procedure for Separator Production

Stoichiometric amounts of powder are mixed together in a polyurethane bottle. The hydration of each chemical is calculated and factored into the amount. Care has to be made to ensure that there are no amalgamates of cerium sulfate powder or ammonium hydrogen phosphate. The chemicals used are:
1. Cerium (III) Sulfate Anhydrate (Alfa Aesar)
2. Ammonium Hydrogen Phosphate (Alfa Aesar)
3. Zirconium Oxide (Tosch)
4. Niobium Oxide (Alfa Aesar)
5. Zirconia mixing balls, approximately one third of the volume of the bottle, are preferably added along with ethanol, or enough to cover the milling media. This bottle is then ball milled, preferably at least 12 hours, followed by a drying cycle in air at an elevated temperature, preferably 30° C.

The powder mixture is then pressed into pellets and calcined on an alumina plate, preferably with a heating profile of 1000° C. for 12 hours, 1,200° C. for 12 hours, and then 1,300° C. for 12 hours with a heating and cooling rate of 5° C./min. The powder is then ground, preferably hand ground in a mortar and pestle, mixed, pressed, and fired again at 1,300° C. for twelve hours to decrease the amount of second phase. This process can also be repeated to further reduce some second phase material. The resulting powder is then hand ground and wet ball milled, preferably for at least 24 hours, to reduce the particle size.

In order to produce a disc, additional processing is necessary. 3 wt % of paraffin wax is dissolved in a beaker with xylene heated preferably to 40° C. NASICON is then mixed into the solution. Next, the mixture is heated and continuously hand stirred until the xylene evaporates. This process coats the powder in paraffin wax and eases pressing but is not necessary to make discs.

Following the waxing process, the powder coated in paraffin wax is weighed and is pressed into a disc using a uniaxial die using an applied at force of preferably 5-6MT for a disk with a diameter of about 3.81 cm and 1.5MT for a disk with a diameter of about 2.54 cm. The discs are then sintered on an alumina plate, preferably at 1,300° C. for 12 hours. After sintering, the surfaces are grinded, preferably using 60 grit grinding paper, to remove any contamination and to roughen the surface. The surface may need to be further roughened by scrapping a piece of alumina or a similarly hard material over the intended electrode area. This process is done to increase the likelihood of adhesion.

A thin layer, preferably approximately 20-30 microns, of platinum ink is applied by a paint brush to an area equal to that of the inner diameter of the intended o-ring to use. A mask is used to give a consistent area. A strip of platinum ink, preferably approximately 5 mm wide, is also painted from the edge of the disc to the electrode. This is later used as an electrical connection. The electrode is applied concentrically on both sides of the disc with the platinum strip on each side deliberately offset from one another. It is air dried and then heated, preferably to 900° C. with no dwell time and more preferably a heating and cooling rate of 5° C./min. Delamination can be minimized by increasing the surface roughness further.

FIG. 2

Figure 2:
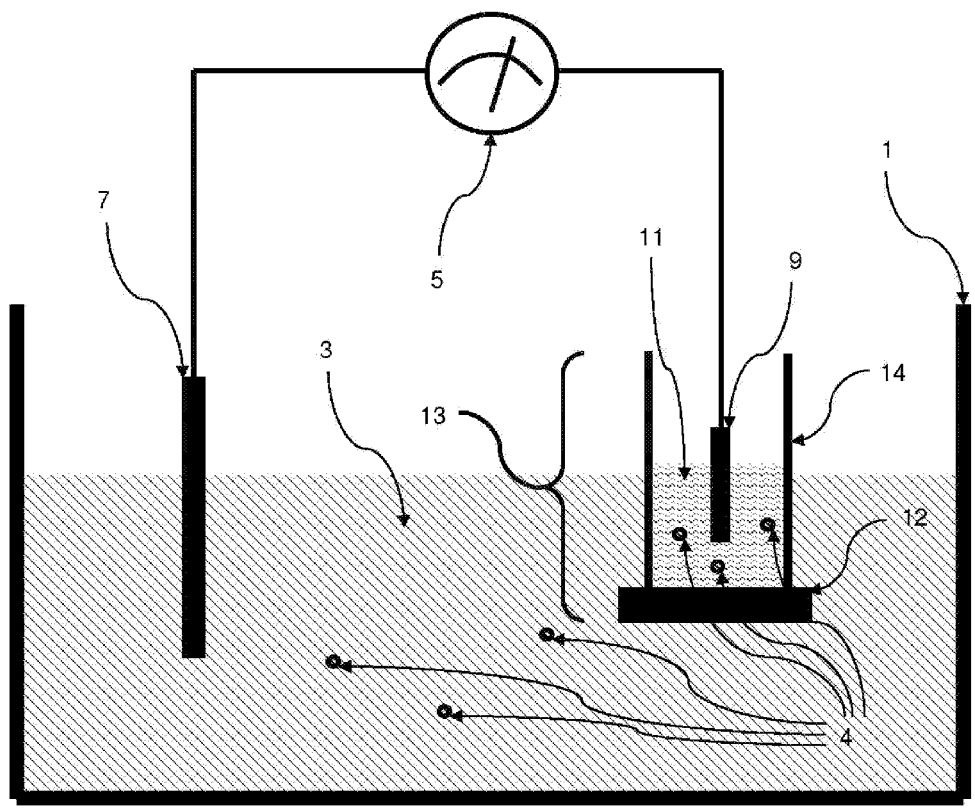
FIG. 2 shows a cross sectional view of one embodiment of the actinide-ion sensor having a separator made from a disk cemented to one open end of a tube.

FIG. 2 shows a cross sectional view of one embodiment of the actinide-ion sensor having a separator 13 made from a disk 12 cemented to one open end of a tube 14. In the embodiment shown in FIG. 2, the container 1, working electrolyte 3, actinide-ion of interest 4, voltmeter 5, working electrode 7, reference electrode 9, and reference electrolyte 11 are as described above.

Separator 13

In this embodiment, the separator 13 is made into a configuration sufficient to separate the reference electrolyte 11 from the working electrolyte 3 while also ionically conductive to the actinide-ion of interest 4. Ionically conductive refers to ionic conduction through all, or a portion, of the separator 13 with respect to the actinide-ion of interest 4.

In this embodiment, the separator 13 is made from two portions, a disk 12 and a tube 14. The separator 13 is formed by cementing the disk 12 to one open end of a tube 14. The reference electrolyte 11 is separated from the working electrolyte 3 by the separator 13. Preferably the disk 12 and a tube 14 of the separator 13 form a vessel having an interior comprising the reference electrolyte 11 and an exterior at least partially contacting the working electrolyte 3. The separator 13 at least partially contacts both the working electrolyte 3 and the reference electrolyte 11. Preferably, the disk 12 contacts the working electrolyte 3. More preferably, the separator 13 is submerged in the working electrolyte 3, so that the disk 12 is fully submerged in the working electrolyte 3, and the tube 14 contacts the working electrolyte 3. Yet more preferably, the separator 13 is submerged in the working electrolyte 3, so that the disk 12 is fully submerged in the working electrolyte 3, and the majority of the tube 14 is submerged in the working electrolyte 3.

In one embodiment, the disk 12 is made of a material comprising an actinide, Zr, and Nb and the tube 14 is made from a material that does not substantially conduct the actinide-ion of interest 4. Preferably, the material that does not substantially conduct the actinide-ion of interest 4 is glass coated $Al_2O_3$. The result is a separator 13 in which substantially all ionic conduction with respect to the actinide-ion of interest 4 occurs through the disk 12.

In an alternative embodiment, both the disk 12 and the tube 14 are made from an actinide-ion of interest 4 conducting material, preferably comprising an actinide, Zr, and Nb. The result is a separator 13 in which ionic conduction with respect to the actinide-ion of interest 4 occurs through portions of the disk 12, portions of the tube 14, or a combination thereof.

In an alternative embodiment, the tube 14 is made of a material comprising an actinide, Zr, and Nb and the disk 12 is made from a material that does not substantially conduct the actinide-ion of interest 4. Preferably, the material that does not substantially conduct the actinide-ion of interest 4 is glass coated $Al_2O_3$. The result is a separator 13 in which substantially all ionic conduction with respect to the actinide-ion of interest 4 occurs through the tube 14.

In an alternative embodiment, the separator 13 is made from a plurality of actinide-ion of interest 4 conductors and actinide-ion of interest 4 substantially non-conductor portions. At least one actinide-ion of interest 4 conductor portion contacts both the working electrolyte 3 and the reference electrolyte 11. Preferably, the material that does not substantially conduct the actinide-ion of interest 4 is glass coated $Al_2O_3$.

FIG. 3

Figure 3:
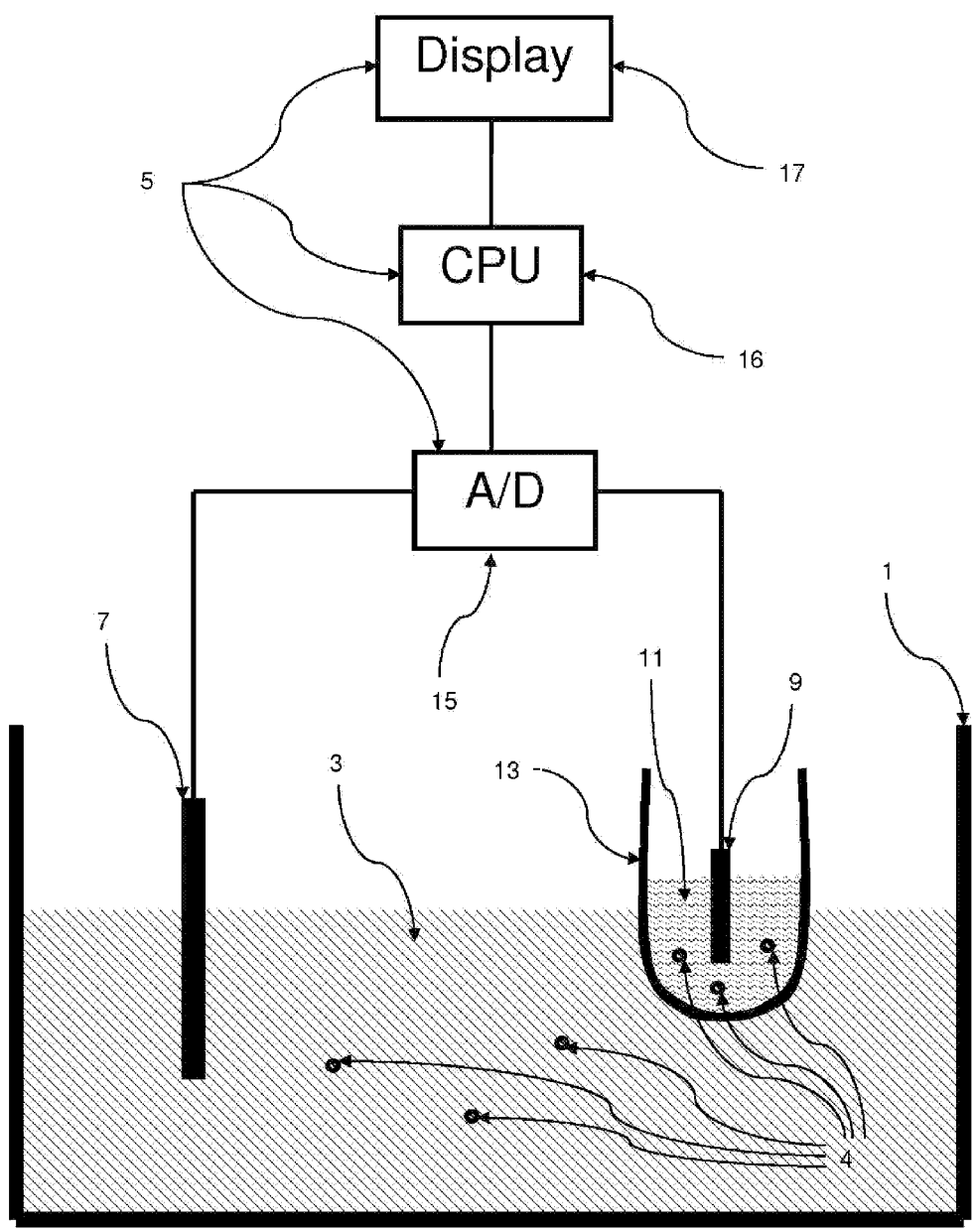
FIG. 3 shows a cross sectional view of one embodiment of the actinide-ion sensor whereby the voltmeter comprises an analog-to-digital converter, a CPU, and a display.

FIG. 3 shows a cross sectional view of one embodiment of the actinide-ion sensor whereby the voltmeter 5 comprises an analog-to-digital converter 15, a central processing unit (CPU) 16, and a display 17, as a means for displaying the actinide-ion of interest 4 concentration. In this embodiment, the container 1, working electrolyte 3, actinide-ion of interest 4, voltmeter 5, working electrode 7, reference electrode 9, reference electrolyte 11, and separator 13 are as described above.

Voltmeter 5

In this embodiment, the voltmeter 5 comprises an analog-to-digital converter 15, a CPU 16, and a display 17. Preferably, the communication between the analog-to-digital converter 15 the CPU 16, and the display 17 is accomplished via one or more wires, busses, wireless communication technologies, etc. In a preferred embodiment, the CPU 16 is connected to the analog-to-digital converter 15 and the display 17 via one or more wires.

CPU 16

The CPU 16 is any means for calculating the actinide-ion of interest 4 concentration in the working electrolyte 3, more preferably a personal computer, a laptop, a microcontroller, or an application-specific integrated circuit (ASIC). Preferably, the CPU 16 comprises a microcontroller having a built-in analog-to-digital converter 15, for example, the microcontroller manufactured by Atmel sold under the trademark ATMEGA128. In an alternate embodiment, the CPU 16 comprises a comparator (e.g. LM339).

The CPU 16 calculates the relative or absolute actinide-ion of interest 4 concentration in the working electrolyte 3 from the voltage measured by the analog-to-digital converter 15. In one embodiment, the calculated actinide-ion of interest 4 calculation is absolute, meaning the actinide-ion of interest 4 concentration in the working electrolyte 3. In an alternative embodiment, the calculated actinide-ion of interest 4 is a relative value, meaning the actinide-ion of interest 4 concentration with respect to a reference solution comprising the actinide-ion of interest 4, or with respect to a specified actinide-ion of interest 4 concentration or concentration range. In one embodiment, the specified actinide-ion of interest 4 concentration or concentration range is coded into the programming. In an alternative embodiment, the specified actinide-ion of interest 4 concentration or concentration range is inputted by the user through a user interference, for example a keyboard, touch screen or dial.

Preferably, the actinide-ion of interest 4 concentration in the working electrolyte 3 is calculated using the Nernst equation, which can be written to relate the measured voltage, E, to the unknown mole fraction of the actinide-ion of interest 4 in the working electrolyte 3, $X_M(WE)$, as shown in Eq. 1:

$$E = E^0 - \left(\frac{RT}{ZF}\right)\ln[\gamma_M^0(WE)] - \left(\frac{RT}{ZF}\right)\ln[X_M(WE)] + A \quad \text{(Eq. 1)}$$

where, $E^0$ is the standard electrode potential for the cell, R is the gas constant, T is the temperature in Kelvin, Z is the charge of the actinide-ion of interest 4, F is Faraday's constant, A is constant, and $\gamma_M^0(WE)$ is activity coefficient of the actinide-ion of interest in the working electrolyte 3. The mole fraction indicates the actinide-ion of interest 4 concentration because it is the number of moles of the actinide-ion of interest 4 over the total moles of the solution.

In an alternative embodiment, the CPU 16 calculates the actinide-ion of interest 4 concentration in the working electrolyte 3 as discussed above, but also compares the calculated concentration value to a target concentration, concentration range, or calibration curve. In one embodiment, the target concentration or concentration range is coded into the programming. In an alternative embodiment, the target concentration or concentration range is input by the user.

In an alternative embodiment, the voltage between the reference electrode 9 and the working electrode 9, detected by the analog-to-digital converter 15 is communicated to the CPU 16. The CPU 16 compares the voltage measurement to a target voltage or specified voltage range. In one embodiment, the target voltage or specified voltage range is coded into the programming. In an alternative embodiment, the target voltage or specified voltage range is input by the user.

Display 17

The CPU 16 communicates the calculated actinide-ion of interest 4 concentration to the display 17 to be displayed. Preferably, the display 17 is a personal computer display, a laptop display, a digital display, an LED display, a segment LED display, one or more LED displays, etc. Preferably, a relative ratio of the actual concentration of actinide-ion of interest 4 to a predetermined maximum, an absolute value of the concentration of actinides of interest 4, or a combination thereof is displayed by the display 17.

In one embodiment, the display 17 is a light that activates, deactivates, or blinks, one or more times, based upon a communication received from the CPU 16. Preferably, the light is an incandescent bulb, an LED, a fluorescent lamp, or similar photon emitting device.

FIG. 4

Figure 4:
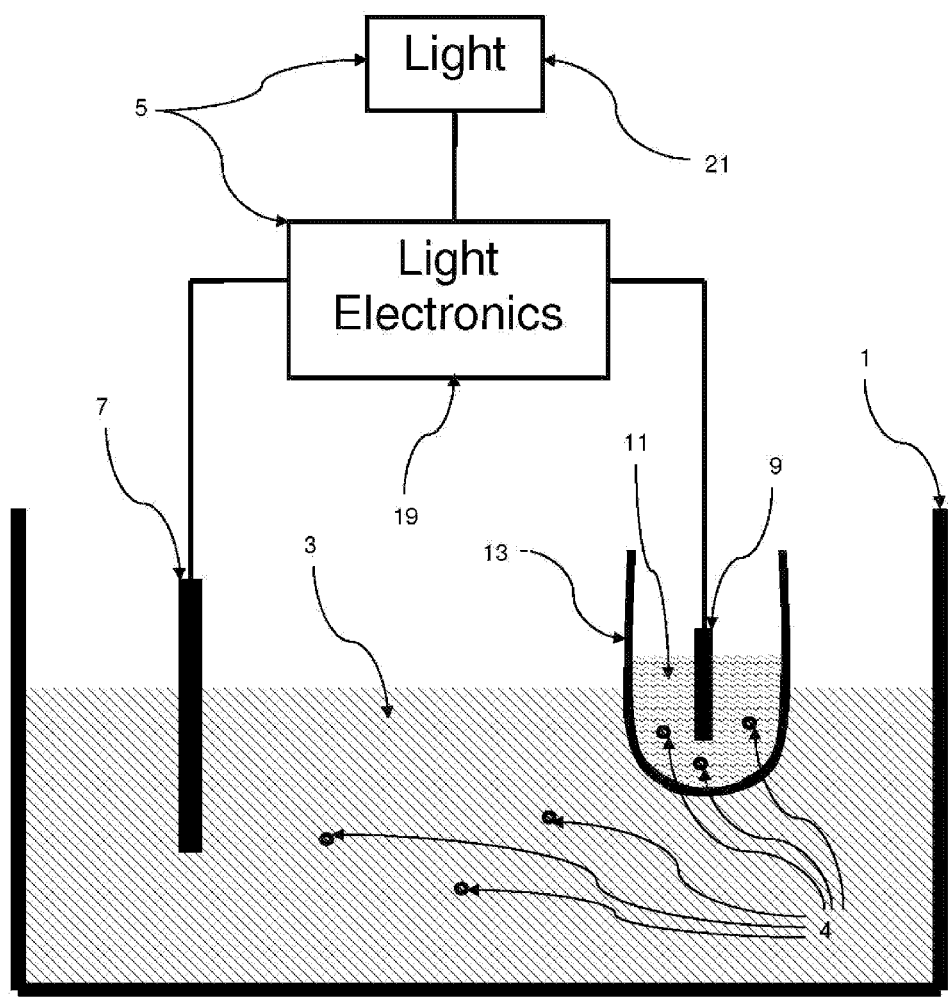
FIG. 4 shows a cross sectional view of one embodiment of the actinide-ion sensor whereby the voltmeter comprises a light.

FIG. 4 shows a cross sectional view of one embodiment of the actinide-ion sensor whereby the voltmeter 5 comprises light electronics 19 and a light 21 to indicate the actinide-ion of interest 4 concentration in the working electrolyte 3. In this embodiment, the container 1, working electrolyte 3, actinide-ion of interest 4, working electrode 7, reference electrode 9, reference electrolyte 11, and separator 13 are as described above.

Light Electronics 19

In this embodiment, light electronics 19 are electrically connected to the working electrode 7, the reference electrode 9, and the light 21. The light electronics 19 provide a high-impedance across the working electrode 7 and reference electrode 9, preferably, using one or more operational amplifiers. In a preferred embodiment, the light electronics 19 comprises a voltage comparator (e.g. LM339).

In one embodiment, a buffered operational amplifier is implemented to provide a high-impedance across the working electrode 7 and reference electrode 9. In a preferred embodiment, an inverting or non-inverting operational amplifier is used to provide a high-impedance across the working electrode 7 and reference electrode 9 while also amplifying the voltage/current to be sufficient for powering the light 21. In one embodiment, the light electronics 19 further comprises a means for amplifying or attenuating the voltage supplied to the light 21, for example, a voltage divider, an operational amplifier, one or more transistors, or a combination thereof.

Light 21

Preferably, the light 21 is an incandescent bulb, an LED, a fluorescent lamp, or similar photon emitting device.

In one embodiment, the light 21 increases in brightness as the actinide-ion of interest 4 concentration decreases in the working electrolyte 3. As the actinide-ion of interest 4 is removed from the working electrolyte 3 during aqueous separation, the actinide-ion of interest 4 concentration decreases while the actinide-ion of interest 4 concentration in the reference electrolyte 11 remains stable. As a result, the voltage increases between the working electrode 7 and the reference electrode 9, increasing the brightness of the light 21 as more of the actinide-ion of interest 4 is removed during aqueous separation. In an alternate embodiment, an inverter circuit provides for an increase light as concentration of the actinide-ion of interest increases. In an alternative embodiment, the light 21 includes a threshold circuit (passive or active that does not supply voltage to the light 21 unless a specified voltage is exceeded. For example, a voltage comparator (e.g. LM 339) or Zener diode connected in reverse polarity may be used to light the light 21 when a predetermined voltage is exceeded. Preferably, one or more resistors creating a voltage divider is used to optimize the circuit.

In a preferred embodiment, user input is used to indicate when the light 21 is toggled on or off. For example, a potentiometer may be used to produce a reference voltage depended on the position of the potentiometer that is feed into a comparator (e.g. LM339) with the voltage between the voltage across the working electrode 7 and reference electrode 9. Preferably, the reference electrode 9 is used as a system ground. Depending on the position of the potentiometer, the light 21 may be power on/off at different actinide-ion of interest 4 concentrations.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

We claim:

1. An apparatus for the real-time monitoring of actinide-ion concentrations, comprising:
   a) a working electrode, a reference electrode, a container, a working electrolyte, a separator, a reference electrolyte, and a voltmeter;
   b) said working electrolyte within the interior of said container;
   c) said working electrolyte separated from said reference electrolyte;
   d) said separator at least partially separating and contacting said working electrolyte and said reference electrolyte;
   e) said working electrolyte at least partially in contact with said working electrode;
   f) said reference electrode at least partially in contact with said reference electrolyte;
   g) said voltmeter electrically connected to said working electrode and said reference electrode
   h) said working electrolyte comprising an actinide-ion of interest;
   i) said separator ionically conductive to said actinide-ion of interest;
   j) said separator comprising an actinide, Zr, and Nb;
   k) said reference electrolyte comprising said actinide-ion of interest with a known concentration;
   l) said voltmeter comprising a means for measuring the voltage between said working electrode and said reference electrode; and
   m) said voltmeter comprising a means for indicating the concentration of said actinide-ion of interest within said working electrolyte.

2. The apparatus of claim 1, whereby said actinide of said separator is an actinide from the list of actinides consisting of Am and Np.

3. The apparatus of claim 1, whereby said actinide of said separator Pu.

4. The apparatus of claim 1, whereby said actinide of said separator is said actinide of interest.

5. The apparatus of claim 1, whereby said separator further comprises P and O.

6. The apparatus of claim 1, whereby said separator consists essentially of an actinide, Zr, Nb, P, and O.

7. The apparatus of claim 1, whereby said separator consists essentially of an actinide, Zr, and Nb.

8. The apparatus of claim 1, further comprising:
   a) said voltmeter having a means for determining the concentration of said actinide-ion of interest within said working electrolyte from said measured voltage between said working electrode and said reference electrode;
   b) said voltmeter comprising a central processing unit, microcontroller, application specific integrated circuit (ASIC), an analog-to-digital converter, a voltage comparator or combinations thereof.

9. The apparatus of claim 1, further comprising:
   a) said working electrode comprises Ta, Pt, W, or a combination thereof; and
   b) said reference electrode comprises Ta, Pt, W, or a combination thereof.

10. The apparatus of claim 1, wherein said working electrolyte comprises nitric acid.

11. The apparatus of claim 1, wherein said separator comprises:
    a) one or more actinide-ion of interest conducting portions; and
    b) said one or more actinide-ion of interest conducting portions comprising an actinide, Zr, and Nb.

12. The apparatus of claim 1, whereby:
    a) said means for measuring the voltage between said working electrode and said reference electrode comprises an analog-to-digital converter;
    b) said means for determining the concentration of said actinide-ion of interest within said working electrolyte comprises a central processing unit;
    c) said means for indicating a concentration of said actinide-ion of interest within said working electrolyte comprises a display; and
    d) said central processing unit connected to said analog-to-digital converter and said display.

13. The apparatus of claim 12, wherein said means for determining the concentration of said actinide-ion of interest within said working electrolyte comprises a means for calculating the concentration of said actinide-ion of interest comprises applying the Nernst equation.

14. The apparatus of claim 1, whereby:
    a) said means for measuring the voltage between said working electrode and said reference electrode and said means for determining the concentration of said actinide-ion of interest within said working electrolyte comprises light electronics;

b) said means for indicating a concentration of said actinide-ion of interest within said working electrolyte comprises a light;

c) said light electronics electrically connected to said reference electrode, said working electrode, and said light; and d) said light electronics comprising a means for supplying a voltage to said light in relation to the actinide of interest concentration in said working electrolyte.

15. The apparatus of claim 1, whereby said actinide of said separator is an actinide from the list of actinides consisting of Am, Np, and Pu.

16. The apparatus of claim 15, further comprising:

a) said working electrode comprises Ta, Pt, W, or a combination thereof; and b) said reference electrode comprises Ta, Pt, W, or a combination thereof.

17. The apparatus of claim 16, wherein said working electrolyte comprises nitric acid.

18. The apparatus of claim 17, wherein:

a) said actinide-ion of interest is Pu;

b) said actinide of said separator Pu; and c) said separator consists of an actinide, Zr, Nb, P, and O.

19. The apparatus of claim 18, said voltmeter comprising:

a) said means for measuring the voltage between said working electrode and said reference electrode comprises an analog-to-digital converter;

b) said means for determining the concentration of said actinide-ion of interest within said working electrolyte comprises central processing unit;

c) said means for indicating a concentration of said actinide-ion of interest within said working electrolyte comprises a display; and d) said central processing unit connected to said analog-to-digital converter and said display.

20. The apparatus of claim 19, wherein said voltmeter comprises:

a) said means for measuring the voltage between said working electrode and said reference electrode and said means for determining the concentration of said actinide-ion of interest within said working electrolyte comprises light electronics;

b) said means for indicating a concentration of said actinide-ion of interest within said working electrolyte comprises a light;

c) said light electronics electrically connected to said reference electrode, said working electrode, and said light; and d) said light electronics comprising a means for supplying a voltage to said light in relation to the actinide of interest concentration in said working electrolyte.

* * * * *